United States Patent
Ruijters et al.

(10) Patent No.: US 11,116,940 B2
(45) Date of Patent: Sep. 14, 2021

(54) X-RAY IMAGING SYSTEM FOR A CATHETER

(71) Applicant: KONINKLIJKE PHILIPS N.V., Eindhoven (NL)

(72) Inventors: Daniel Simon Anna Ruijters, Eindhoven (NL); Sander Hans Denissen, Veldhoven (NL); Michael Grass, Buchholz In der Nordheide (DE); Erik Martinus Hubertus Petrus Van Dijk, Den Bosch (NL); Dirk Dijkkamp, Waalre (NL); Maikel Hendriks, Roermond (NL); Erik Rene Kieft, Eindhoven (NL); Marco Verstege, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1030 days.

(21) Appl. No.: 14/432,228

(22) PCT Filed: Oct. 2, 2013

(86) PCT No.: PCT/IB2013/059055
§ 371 (c)(1),
(2) Date: Mar. 30, 2015

(87) PCT Pub. No.: WO2014/057393
PCT Pub. Date: Apr. 17, 2014

(65) Prior Publication Data
US 2015/0250983 A1 Sep. 10, 2015

Related U.S. Application Data

(60) Provisional application No. 61/711,272, filed on Oct. 9, 2012.

(51) Int. Cl.
*A61M 25/01* (2006.01)
*A61B 6/12* (2006.01)
(Continued)

(52) U.S. Cl.
CPC .......... *A61M 25/0116* (2013.01); *A61B 6/12* (2013.01); *A61B 34/30* (2016.02); *A61B 90/37* (2016.02);
(Continued)

(58) Field of Classification Search
CPC .............. A61M 25/00; A61M 25/0116; A61M 25/0108; A61M 25/0147; A61B 6/12;
(Continued)

(56) References Cited

U.S. PATENT DOCUMENTS 6,493,575 B1 * 12/2002 Kesten ................... A61B 90/36
600/431
8,046,054 B2 10/2011 Kim et al.
(Continued)

FOREIGN PATENT DOCUMENTS

| WO | 2011057260 A2 | 5/2011 |
|---|---|---|
| WO | 2011095927 A1 | 8/2011 |

*Primary Examiner* — Sean D Mattson (57) ABSTRACT

The invention addresses the problem of correctly positioning a catheter and reducing radiation doses. It relates to an X-ray imaging system (1) for a robotic catheter, comprising said catheter (3), and a processing unit (5) for receiving X-ray images of a patient environment (15). By being adapted to receive one or more auxiliary information items and using said information for determining the catheter position, the processing unit does not entirely have to rely on a large number of scanned image data, thus helping to reduce radiation while correctly delivering the catheter position as a function of as few as a single image, preferably 2D, and said one auxiliary information items. Further, said processing unit allows for at least one of rendering an image and provide said image to a visualization device (21), and
(Continued)

providing feedback, e.g. steering commands, to said robotic catheter.

24 Claims, 4 Drawing Sheets

(51) Int. Cl.
    *A61B 34/30*     (2016.01)
    *A61B 90/00*     (2016.01)
(52) U.S. Cl.
    CPC .... *A61M 25/0108* (2013.01); *A61M 25/0147* (2013.01); *A61B 2034/301* (2016.02); *A61B 2090/376* (2016.02); *A61B 2090/3966* (2016.02)
(58) Field of Classification Search
    CPC ... A61B 34/30; A61B 90/37; A61B 2034/301; A61B 2090/376; A61B 2090/3966
    See application file for complete search history.

(56) References Cited

U.S. PATENT DOCUMENTS

| | | |
|---|---|---|
| 8,396,533 B2 | 3/2013 | Barbu et al. |
| 8,684,962 B2 | 4/2014 | Kirschenman |
| 9,095,349 B2 | 8/2015 | Fish et al. |
| 2003/0014034 A1* | 1/2003 | Strobel ............... A61B 6/12 604/407 |
| 2005/0256398 A1 | 11/2005 | Hastings et al. |
| 2006/0058647 A1* | 3/2006 | Strommer ............ A61B 5/06 600/434 |
| 2006/0153468 A1 | 7/2006 | Solf |
| 2006/0200026 A1 | 9/2006 | Wallace et al. |
| 2007/0073151 A1 | 3/2007 | Lee |
| 2007/0189457 A1* | 8/2007 | Deinzer ............... A61B 6/12 378/98.12 |
| 2008/0043902 A1 | 2/2008 | Viswanathan |
| 2009/0093712 A1* | 4/2009 | Busch ................. A61B 5/06 600/424 |
| 2009/0182226 A1 | 7/2009 | Weitzner et al. |
| 2010/0056904 A1* | 3/2010 | Saunders ............. A61B 6/12 600/424 |
| 2010/0256558 A1* | 10/2010 | Olson .............. A61M 25/0147 604/95.01 |
| 2011/0077504 A1 | 3/2011 | Fischer et al. |
| 2011/0230758 A1* | 9/2011 | Eichler ............... A61B 5/06 600/424 |
| 2011/0295111 A1 | 12/2011 | Hansis et al. |
| 2012/0004533 A1 | 1/2012 | Peng et al. |
| 2012/0071751 A1* | 3/2012 | Sra .................... A61B 6/12 600/424 |
| 2012/0158012 A1 | 6/2012 | Sandhu et al. |

\* cited by examiner

X-RAY IMAGING SYSTEM FOR A CATHETER

CROSS-REFERENCE TO PRIOR APPLICATIONS

This application is the U.S. National Phase application under 35 U.S.C. § 371 of International Application Serial No. PCT/IB2013/059055, filed on Oct. 2, 2013, which claims benefit of U.S. Application No. 61/711,272, filed on Oct. 9, 2012. These applications are hereby incorporated by reference herein.

FIELD OF THE INVENTION

The invention relates to an X-ray imaging system for detecting the position and orientation of a robotic catheter inside a patient environment. The invention further relates to a method of determining the position and orientation of a robotic catheter inside the patient environment. Still further, the invention relates to the use of the system for determining the orientation and position of the catheter and a computer program for performing the method.

BACKGROUND OF THE INVENTION

U.S. Pat. No. 8,046,054 B2 discloses an X-ray fluoroscopic imaging system mounted on a ring frame cooperating with a surgical robot. The patent addresses three-dimensional modeling of surgical instruments based on bi-planar imaging. Navigation of the surgical robot is allegedly accomplished by using a pre-planned path of movement and the three-dimensional model. A general problem related to known imaging systems which rely on fluoroscopy is that the patient is subjected to a large dosage of X-ray radiation, leading to an increased risk of cell damage.

The bi-planar imagining system uses relatively high radiation doses, which is perceived as disadvantageous. A further problem unsolved by the prior art is the circumstance that the catheter may possess an unknown amount of torque upon entry of the patient's body and is flexible which makes it all the more difficult to correctly assess its position and orientation.

SUMMARY OF THE INVENTION

It is an object of the invention to provide an X-ray imaging system for a robotic catheter which allows for correct and reliable determination of the orientation and position of the catheter while limiting the patient's exposure to X-ray radiation.

It is a further object of the invention to provide a method of determining the orientation and position of a robotic catheter inside a patient which provides for correct and reliable determination of the orientation and position of the catheter while limiting the patient's exposure to X-ray radiation.

In a first aspect of the present invention an X-ray imaging system for a robotic catheter is presented, the system comprising a robotic catheter and a processor, the processor being connectable, preferably through a first data interface, to an X-ray image data source for receiving X-ray image data, preferably two-dimensional X-ray image data, of a patient environment. The processor further is connectable, preferably through a second data interface, to the robotic catheter, wherein the processor is adapted to a) receive one or more auxiliary information items received from at least one of the data source, preferably through the first data interface, and the catheter, preferably through the second data interface, b) determine a set of possible three-dimensional orientations and positions of the catheter (relative to the patient environment) as a function of the, preferably two-dimensional, image data and the one or more auxiliary information items. Further, the processor is adapted to perform at least one of:

c) rendering an image of at least one of the set of possible orientations and positions of the catheter, and at least one of the, preferably two-dimensional, image data, and a three-dimensional representation of the patient environment, and providing the image to a visualization device; and d) providing feedback to the robotic catheter, the feedback being a function of the set of possible orientations and positions.

The X-ray image data source preferentially is a C-arm apparatus, and could alternatively also be a computed tomography apparatus.

If an image is rendered with respect to a three-dimensional representation of a patient environment, preferably the representation is provided in digital form either by the image data source directly or by means of conventional data storage means. The three-dimensional representation may have been provided by previously scanning the patient environment.

A central benefit of the invention is that while it would also work when using three-dimensional data as data input for the first data interface, detection of orientation and position of the catheter is enabled already on the basis of one single or multiple two-dimensional X-ray images. Instead of multiple further patient scans using X-ray radiation, auxiliary information items are provided to the processor through the second data interface which may be used by the processor to determine the orientation and position of the catheter. These auxiliary information items are provided without further X-ray scanning, thus lowering the radiation dosage submitted to the patient environment. Based upon this information, a set of orientations and positions is obtained. A set of orientations may comprise one or more orientations and positions of the catheter. Once the position and orientation of the catheter has been determined, the processor can be used to visualize the catheter alone, or in combination with a two- or in a three-dimensional representation of the patient environment. With the aid of this visualization, the system can provide feedback for the robotic catheter as a function of the catheter orientation and position. The feedback may be triggered by user input or may be automatically generated by the processor.

Preferably, the auxiliary information items represent at least one of: curvature of a portion of the catheter or of the entire catheter, a steering command previously transmitted to the catheter, a previous orientation/position/curvature of the catheter, a force feedback signal detected and transmitted by the catheter, and anatomical boundary information from a patient's three-dimensional model. The curvature of a catheter, or of a portion thereof, may be determined by analyzing the current steering setting of the catheter. Optionally, force feedback signals detected and transmitted by the catheter are considered for predicting the catheter curvature. Force feedback signals are in particular detected when the catheter due to its curvature setting touches a boundary wall of the patient environment, for instance a blood vessel wall. Once predicted, the curvature of the catheter can be matched by the processor to the curvature of the catheter as rendered in the image by the processor. Applying this curvature-matching technique will deliver one, two or a limited number of possible sets of position and orientation of the catheter. From the aforementioned it is clear that the auxiliary information items also provide for accurate determination of the orientation and position of the catheter. In particular the use of catheter-related information items such as curvature, previous position and steering commands of the catheter jointly or separately eliminates the uncertainty involved with initial torque and skew present along the catheter upon insertion into the body. The use of force-feedback signals and anatomical boundary conditions eliminates the uncertainty involved with an unknown deviation of the catheter's orientation from what the steering controls would effect when the catheter is in an "unbound" environment i.e. outside of the patient and unrestricted. Overall precision in determining the catheter position and orientation is achieved.

Preferably, the auxiliary information items represent at least one of a steering setting, previously transmitted to the catheter, and previous orientation/position/curvature of the catheter. By consideration of previously determined parameters such as the aforementioned, the system is able to select the most probable orientation and position for the catheter among the set of possible orientations and positions. This may be done by eliminating those orientations and positions from the set which deviate too significantly from the previously established positions and orientations to have likely been achieved by ordinary navigation of the catheter.

The most probable orientation is selected by respectively taking the previously established curvature of the catheter, i.e. pose, into account and is preferentially determined using a similarity measure. Thus, the processor identifies one pose out of the set of possible orientations and positions which is most temporally consistent with the previously established pose. The pose with the highest similarity measure is then selected. One preferred similarity measure is performed by generating the sum of euclidian distances for each point in the test pose and their closest counterpart in the previously established pose.

Preferentially, at the system comprises an input device adapted to receive user input, the user input representing a user choice of one out of the set of possible orientations and positions of the catheter displayed by the visualization device. This embodiment enables the user to manually confirm or select one of several orientations and positions suggested by the system.

The user input preferentially represents one or more commands for moving the catheter. The commands for moving the catheter are preferentially displayed in display— or image—coordinates and may be entered by the user for example as commands to bend left, right, up, down, front or back, all with respect to the image which is being displayed. the user input to the processor, the processor being adapted to process the user input into a set of steering commands, and the feedback being to provide the set of steering commands to the robotic catheter. The steering commands which are to be relayed to the robotic catheter are translated by the processor from the input "display" coordinates into "world" coordinates, i.e. coordinates in the catheter system.

Alternatively, the processor is adapted preferentially to process the three-dimensional orientation and position of the catheter, once established, relative to the patient environment as a function of the two-dimensional image data and the one or more auxiliary information items into a set of steering commands, wherein the feedback is to provide the set of steering commands to the robotic catheter. In case the orientation and position of the catheter is determined without user input being necessary, and in case the catheter navigation is predetermined, for example by a planning software, the system in this embodiment automatically feeds back steering information to the robotic catheter for advancing on the pre-planned path.

It is preferred that the catheter tip is adapted to perform small movements along a predetermined path, and the processor is adapted to detect the movements from a series of two-dimensional X-ray image data or the patient environment and to deduct herefrom the orientation of the catheter. The series of X-ray image data is preferentially obtained through the X-ray image data source, e.g. a C-arm. The serial detection of small movements of the catheter tip, the so-called catheter wiggle, enables the system to determine which orientation and position of the catheter is the most probable among the set of possible orientations and positions. This is especially true for situations in which the curvature of the catheter is (essentially) parallel to the viewing plane, i.e. the two-dimensional X-ray image. It is then difficult to robustly select the most likely of the several plausible solutions.

Preferentially, the system is adapted to provide feedback to the user of this uncertainty and to propose either to select a different view (i.e. different scanning angle) or to apply catheter wiggling for resolving the inconsistency. Under a "small" movement, such a movement of the catheter tip is understood which is smaller than the confining space surrounding the catheter tip. As confining space, inter alia the vessel diameter or heart chamber volume may be considered.

Preferably, the catheter movement, also referred to as "catheter wiggle", is at first performed in a first plane of movement one or more times, and afterwards, a catheter movement is performed in a second plane which is oriented in an angle with respect to the first plane of movement. If required, it is preferred to repeat this two-step procedure, preferably under variation of the angle between first and second plane. The result herefrom is seen in the projected image, which will indicate differing amplitudes for differing rotation planes and allows calculation of the catheter orientation.

In a preferred embodiment, the catheter tip comprises multiple radio-opaque markers which are arranged along the tip, preferably in a fixed spatial relation to the wires for sealing the catheter in order to deduct herefrom the orientation of the catheter.

According to a first preferred alternative, the markers are arranged symmetrically along the tip of the catheter.

According to a second preferred alternative, the markers are arranged asymmetrically along the tip of the catheter.

Optionally, also the steering wires of the catheter are provided with multiple radion-opaque markers. The effect of adding these assymetric markers to the catheter tip, and optionally the catheter, is that the steering wire which is being actuated to achieve curvature of the catheter can be related to the catheter in the two-dimensional X-ray image. Due to the asymmetry it can be determined from the image if the marker is on the source side or on the detector side of the catheter, the source side specifying that side of the catheter which is closer to the source of radiation, and the detector side being opposite thereof. This allows for determining whether the pulled steering wire causes movement of the catheter tip towards or away from the radiation source.

In a preferred embodiment, the processor is adapted to initialize the aforementioned procedures of determining the pose of the catheter based upon two or more two-dimensional images obtained by the image data source and to subsequently register, i.e. track the orientations and positions being determined.

Preferentially, the first data interface, by way of which the processor is adapted to communicate with the robotic catheter, is adapted to provide steering commands to the X-ray image data source, the steering commands being a function of the orientation and position of the catheter.

According to a further aspect of the invention, a method of determining the position and orientation of a robotic catheter inside a patient environment is presented, wherein the method comprises the steps of obtaining X-ray image data, in particular two-dimensional image data, of the patient environment and the catheter, from an X-ray image data source a) obtaining one or more auxiliary information items from at least one of the catheter and the image data source, b) determining a set of possible three-dimensional orientations and positions of the catheter relative to the patient environment as a function of the, preferably two-dimensional, image data and the auxiliary information item or items, and at least one of:

c) rendering an image of the set of possible orientations and positions of the catheter and at least one of the, preferably two-dimensional, image data and a three-dimensional representation of the patient environment and providing the image to a visualization device; and d) providing feedback to the robotic catheter, the feedback being a function of the set of possible orientations and positions.

With regard to the benefits and advantages embodiments of this method, it is referred to the benefits and embodiments of the system according to the invention presented hereinabove.

In particular, it is preferred that the set of possible three-dimensional orientations and positions of the catheter relative to the patient environment is determined by use of information representing at least one of:

the curvature of the catheter, or of a portion of the catheter, a steering command previously transmitted to the catheter, a previous orientation of the catheter, a previous position of the catheter, a previous curvature of at least a portion of the catheter, a force feedback signal detected and transmitted by the catheter, and anatomical boundary information from a patient's three-dimensional model.

Further, the method preferably comprises one, several or all of the steps of:

registering user input, the user input representing at least one of a user choice of one out of the set of possible orientations and positions of the catheter, and one or more commands for moving the catheter;

processing the user input into a set of steering commands for the catheter;

providing the set of steering commands to the catheter.

Preferentially, the method according to the invention further comprises one, several or all of the steps of processing the three-dimensional orientation and position of the catheter relative to the patient environment as a function of the, preferably two-dimensional, image data and the one or more auxiliary information items into a set of steering commands, and providing the set of steering commands to the robotic catheter.

It is preferred that the method according to the invention comprises one, several or all of the steps of performing small movements of the catheter tip along a predetermined path, detecting the movements in a series of X-ray image data, and deducting the catheter orientation from the movements.

In a further aspect of the present invention, a use of an X-ray imaging system for a robotic catheter is presented for determining the orientation and position of the catheter inside a patient environment, wherein the system is a system according to one of the preferred embodiments of the invention described hereinabove.

In a further aspect, a computer program for operating an X-ray imaging system according to the invention as described hereinabove, in particular according to one of claims 1 to 10 is presented, the computer program comprising program code means for performing the method steps of the method of determining the orientating and position of a robotic catheter inside a patient environment according to the invention as described hereinabove, in particular according to one of claims 10 to 13, when the computer program is run on a computer controlling the X-ray imaging system and comprising the processor unit.

It shall be understood that the X-ray imaging system according to the invention, in particular of one of claims 1 to 9, the method according to the invention, in particular of one of claims 10 to 13, the use according to the invention, in particular of claim 14 and the computer product according to the invention, in particular of claim 15, have similar or identical preferred embodiments, in particular, as defined in the dependent claims.

It shall further be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

Figure 1:
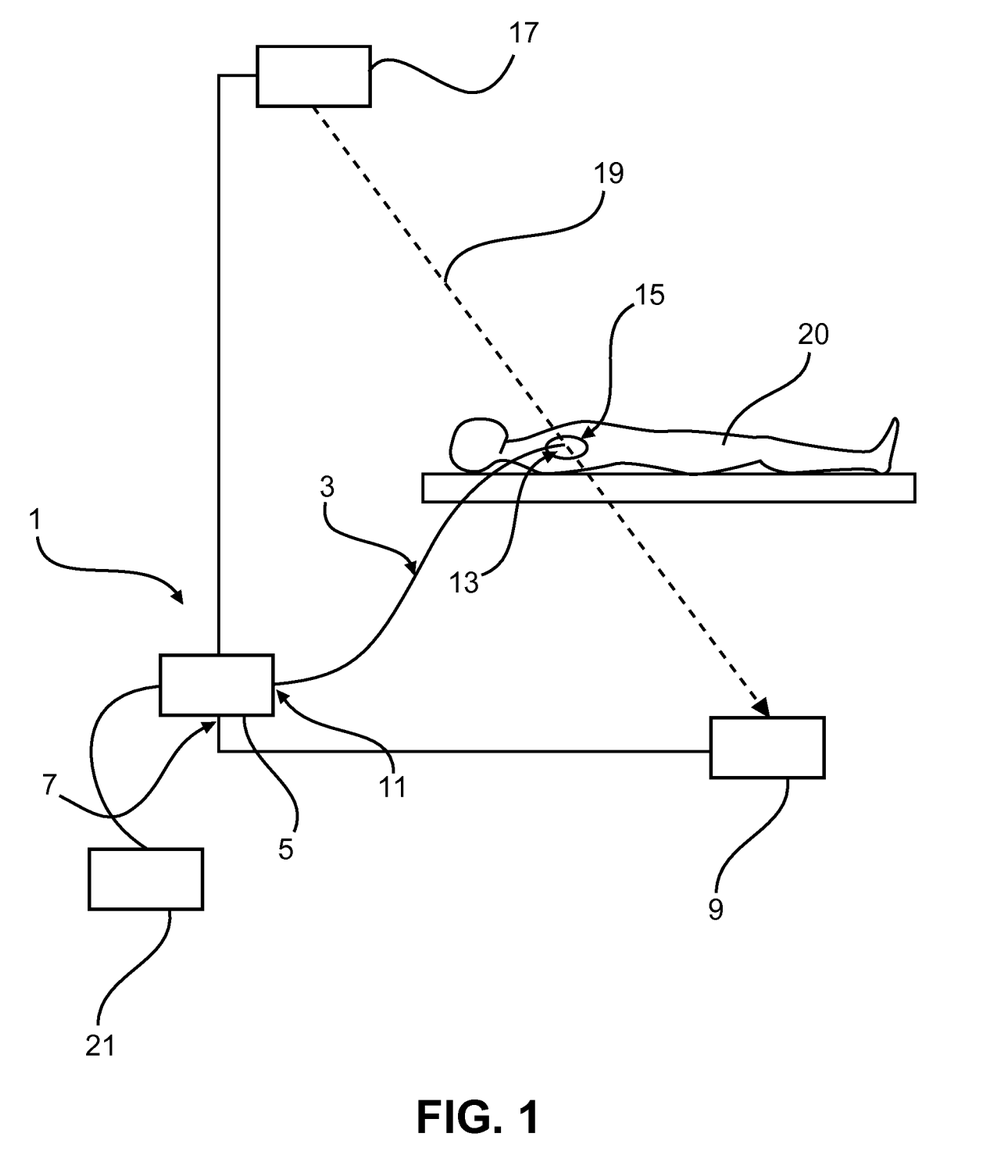
FIG. 1 shows schematically and exemplarily an embodiment of an X-ray imaging system.

FIG. 1 shows an X-ray imaging system 1 according to the invention. The X-ray imaging system 1 comprises a robotic catheter 3 and a processor 5. The processor 5 is connected to an X-ray image data source 9 through a first data interface 7. The X-ray image data source 9 is an X-ray detector in this embodiment. The robotic catheter 3 is connected to the processor 5 through a second data interface 11. The processor 5 is further connected to an X-ray source 17 which is adapted to emit X-rays 19 towards the X-ray image data source 9. Positioned in between the X-ray source 17 and the image data source 9 is a patient 20. The patient 20 comprises a region through which the X-rays 19 pass the body of the patient 20. This region is denominated patient environment 15. The robotic catheter 3 comprises a catheter tip 13 which is in the state according to FIG. 1 introduced into the patient environment 15 of the patient 20.

The processor 5 according to FIG. 1 is further connected to a visualization device 21. Optionally, an input device (not shown) is connected to the processor 5. The visualization device 21 and the input device may be integrated into one device, for example comprising a touch screen. The X-ray imaging system 1 optionally comprises at least one of the visualization device 21, the image data source 9, the X-ray source 17 and the input device to form an integrated system.

In operation of the X-ray imaging system 1, the X-ray source 17 emits X-rays 19 which pass through the patient environment 15 and are recorded by the image data source 9. In addition to anatomical information of the patient 20, the image data source 9 also records geometrical information of the catheter inside the patient environment 15. Image data is transmitted from the image data source 9 through the first data interface 7 to the processor 5. Furthermore, auxiliary information items in the form of information representing at least one of the curvature of the robotic catheter 3, steering commands previously transmitted to the robotic catheter 3, and force feedback signals detected and transmitted by the robotic catheter 3 are transmitted from the robotic catheter 3 to the processor 5. The robotic catheter 3 is either directly coupled to the processor 5 or coupled to a catheter control device (not shown) which in turn is connected to the processor 5 for data communication.

The processor 5 uses as many auxiliary information items as necessary for determining the curvature of the robotic catheter 3. Additionally, the processor 5 matches the curvature of the catheter, once determined, to the image data transmitted from the image data source 9. Once the curvature has been successfully mapped to the image data, or at least once a set of possible orientations and positions of the catheter with respect to the image data have been established, an image of the catheter and at least one of the, preferably two-dimensional, image data and a three-dimensional model of the patient environment and the catheter are rendered and transmitted to the visualization device 21. The three-dimensional model of the patient environment is preferentially supplied in a previous scanning procedure under use of the X-ray source 17 and the image data source 9 or through data storage means.

Figure 2:
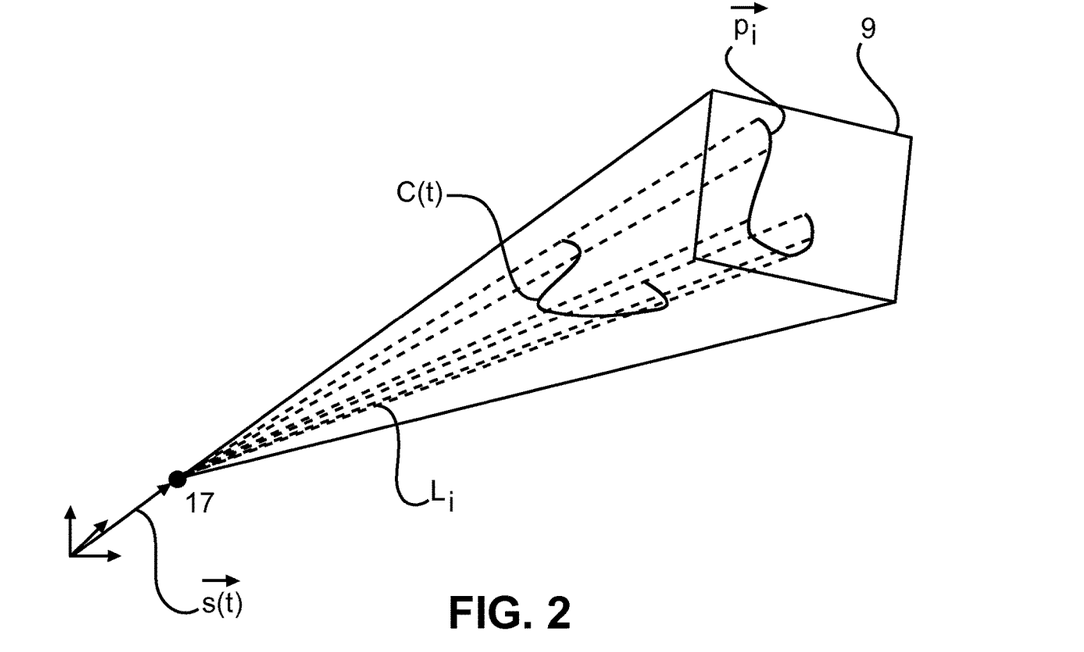
FIG. 2 shows schematically and exemplarily a projection of a catheter pose on an X-ray detector.

FIG. 2 schematically depicts a preferred way of matching the curvature of the robotic catheter 3 to the image data detected by the image data source 9. In FIG. 2, C(t) is the specific description of the curved catheter, called pose, in a given coordinate system. C(t) is obtained from the auxiliary information items as described herein-above. $\vec{p}_i$ is a set of points representing the projection of the detected catheter on an X-ray image of the image data source 9. $\vec{s}$ is the vector leading from the center of the coordinate system to the point of emission of the X-ray source. From the X-ray source, a set of lines $L_i$ are emitted towards the image data source 9. $L_i$ is determined as $$L_i = \vec{s} + \tau \cdot (\vec{p}_i - \vec{s}).$$

Herein, $\tau$ is a scaling variable employed to describe a straight line from $\vec{s}$ ($\tau$ is 0) to $\vec{p}_i$ ($\tau$ is 1).

The coordinates of $\vec{s}$, and the coordinates of the projection $\vec{p}_i$ are known to the processor. What is not known and has to be determined is the orientation and position of C(t) in the coordinate system. The processor 5 is adapted to transpose, i.e. move the known curvature C(t) within the coordinate system until its projection along $L_i$ resembles the shape of the projection in the plane of the image recorded by the image data source 9. In addition, by varying the distance between the curvature C(t) and the source of radiation, due to the conical orientation of the rays $L_i$ the position of the curvature with respect to the size ratio shown on the projection $\vec{p}_i$ may be varied. In mathematical terms, what the processor 5 does is minimizing the distance between C(t) and the set of lines $L_i$, along the algorithm $$L_i: \arg\min \operatorname{dist}(C(t), L_i).$$

Following this approach will lead to one or more minima which represent plausible solutions to the algorithm and thus represent a set of possible orientations and positions of the catheter in the coordinate system.

Figure 3:
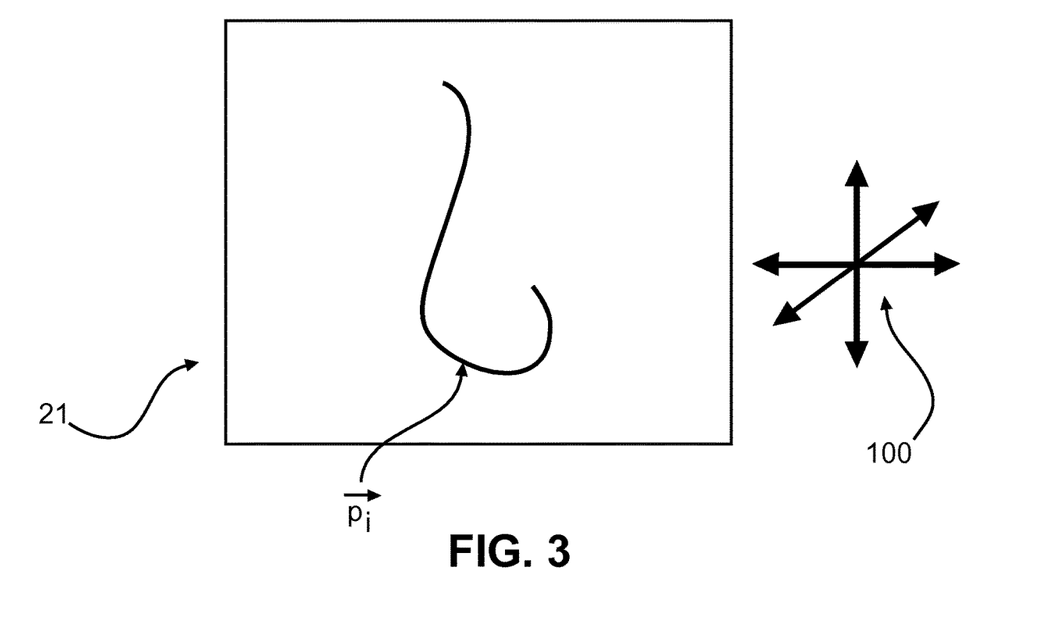
FIG. 3 shows schematically and exemplarily a user input with respect to an X-ray image.

FIG. 3 shows a schematic visualization of the catheter projection of FIG. 2 on a display. A coordinate system indicates options for user input 100 in three dimensions. The user can input steering commands based upon the two-dimensional view which is being displayed. The processing unit adapted to translate the user input from the coordinates in the image plane, which is the plane of the detector, into the coordinates of the catheter system and generate a set of steering commands which will cause the catheter to move in the three-dimensional catheter coordinate system. In those embodiments in which the catheter contains radio-opaque markers which preferably are located asymmetrically on the catheter, the marker detection in the X-ray image being displayed can help determine the pose of the catheter, or help determine which plausible solution of the set of possible orientations and positions is most likely. In a closed feedback loop it will further be possible to move the X-ray source 17 (FIG. 1) to a different viewing angle relative to the patient environment 15 which is selected as a function of the catheter orientation and position in case the latter is changed during the use of the catheter.

The method according to the invention is described hereinafter with reference to FIGS. 4 through 6.

Figure 4:
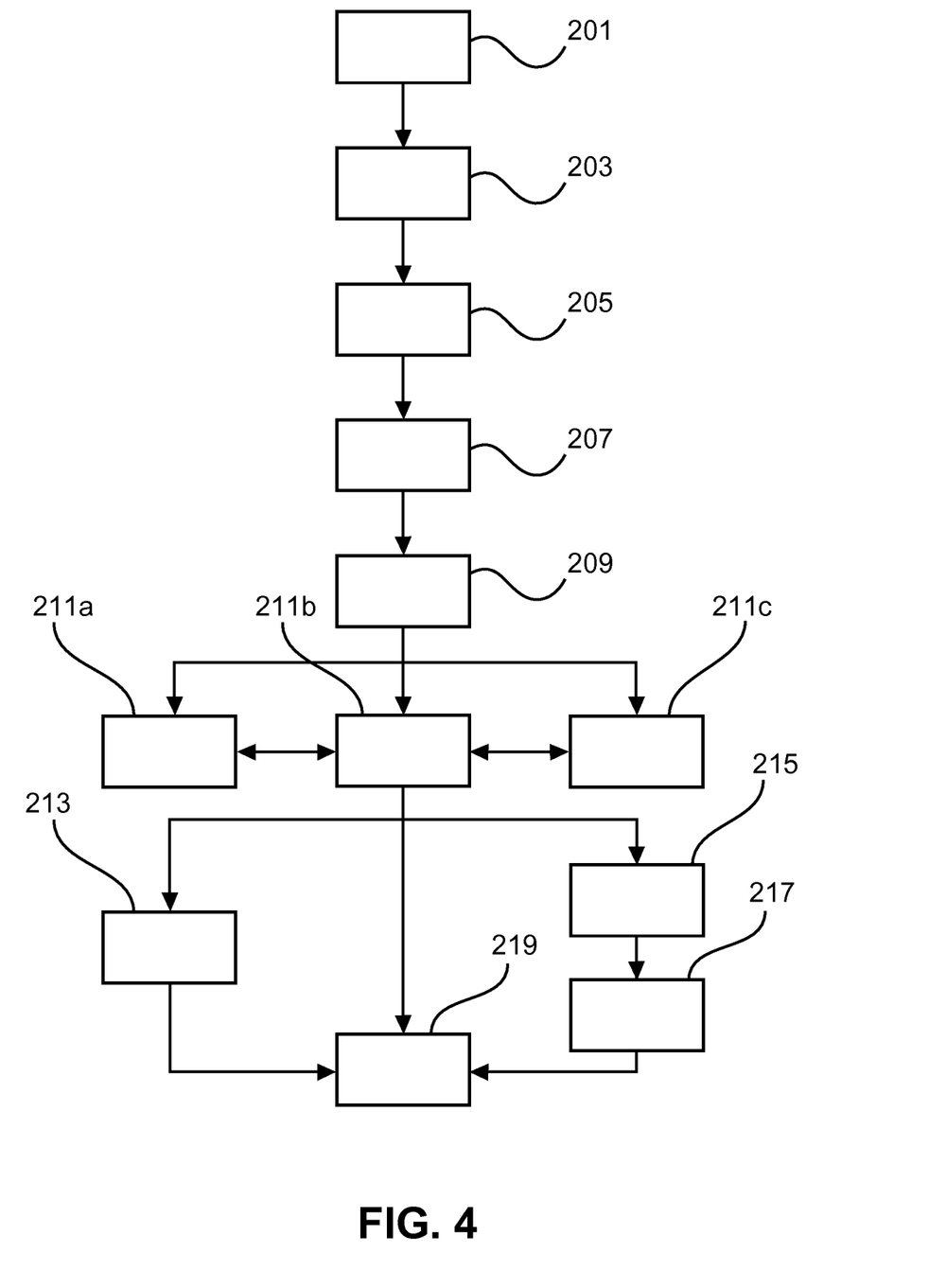
FIG. 4 shows schematically and exemplarily a flow chart of a method of determining the position and orientation of a robotic catheter.

FIG. 4 shows a flow chart of a method for determining the orientation and position of a catheter inside a patient environment. In step 201, a robotic catheter is introduced into the body of a patient, in particular into the patient environment. In step 203, X-ray image data is obtained, in particular two-dimensional image data from the patient environment and the catheter. Preferably, this is done with an X-ray image data source.

In step 205, one or more auxiliary information items are obtained from the catheter and/or the image data source.

In step 207, a set of possible three-dimensional orientations and positions of the catheter relative to the patient environment are determined as a function of the, preferably two-dimensional, image data and the auxiliary information item or items.

Figure 6:
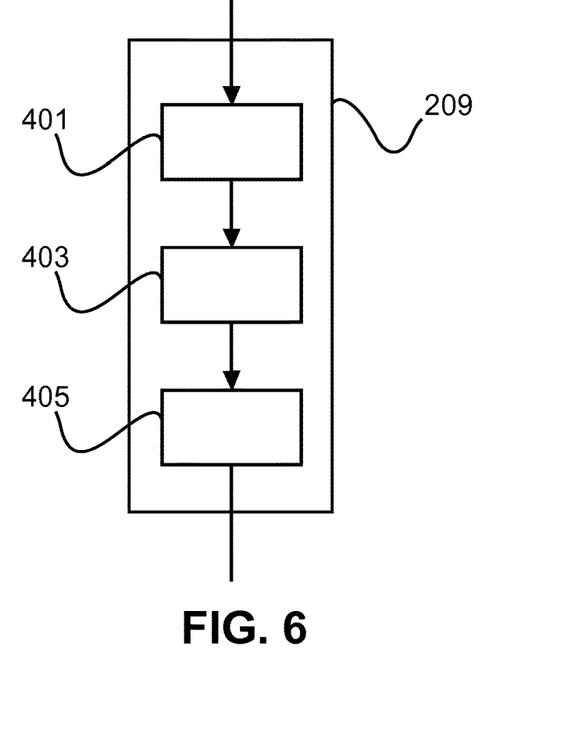
FIG. 6 shows schematically and exemplarily a further detail flow chart according to FIG. 4.

In step 209, the set of possible orientations and positions is reduced to one definite orientation and position of the catheter by performing the procedure of catheter wiggling (FIG. 6, described hereinabove and hereinafter).

After establishing at least the set of possible orientations and positions of the catheter, in step 211a an image of the set of possible orientations and positions of the catheter is rendered. Alternatively or additionally, in step 211b an image of the two-dimensional image data is rendered. Alternatively or additionally, in step 211c an image of a three-dimensional representation of the patient environment is rendered. Steps 211a-c may be performed simultaneously or jointly. In step 213, the three-dimensional orientation and position of the catheter is being processed relative to the patient environment as a function of the two-dimensional image data and the one or more auxiliary information items into a set of steering commands, and the steering commands are provided to the robotic catheter in step 219. Alternatively or additionally, in step 215 the image is provided to a visualization device. Alternatively or additionally to step 213 and 215, feedback is provided immediately to the robotic catheter, the feedback being a function of the set of possible orientations and positions.

Figure 5:
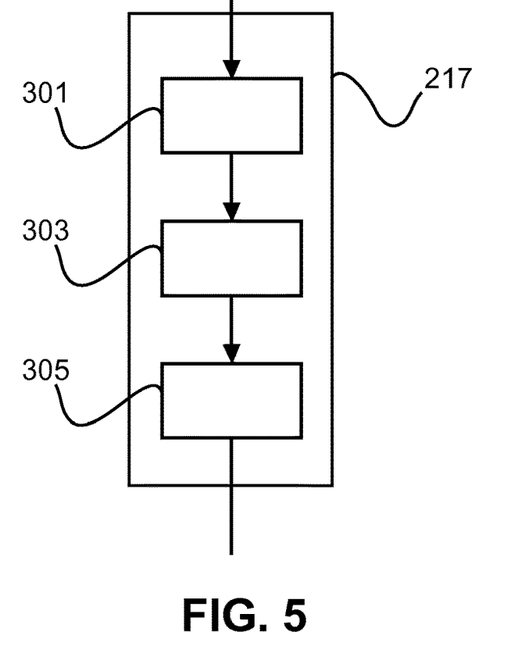
FIG. 5 shows schematically and exemplarily a detail of the flow chart according to FIG. 4.

Following step 215, if performed, preferably the steps as shown in FIG. 5, are followed through. FIG. 5 shows the substeps of step 217. At first, in step 301 user input is registered, wherein the user input represents a user choice of one out of the set of possible orientations and positions of the catheter, and/or one or more commands for moving the catheter.

Step 303 consists of processing the user input into a set of steering commands for the catheter, and in step 305, the set of steering commands is provided to the catheter, leading to step 219.

FIG. 6 shows in more detail the method step of the "catheter wiggle" procedure. Herein, at first small movements of the catheter tip are performed along a predetermined path in step 401. Preferably, the catheter tip is at first moved in a first plane for a predetermined number of times, before it is moved in a second plane for a predetermined number of times. The first plane and second plane are oriented in an angle relative to each other.

Step 401 may be repeated multiple times, until the orientation and position of the catheter has been successfully and definitely been determined. Herein, it is preferred if the angle between the first plane and second plane of movement of the catheter tips varies with each repetition.

In step 403, the movements performed by the catheter tip are respectively detected in a series of X-ray image data. In step 405, the catheter orientation is deducted from the movements.

The system and method described herein-above are provided for use in endovascular interventional treatment, such as AAA-procedures, TAVI procedures, EP procedures, structural heart disease procedures and others.

Procedures like the determination of the catheter orientation and position, the obtaining of X-ray image data, obtaining one or more auxiliary items, rendering of images, providing feedback to the catheter, registering user input, processing the input into steering commands for the catheter, et cetera performed by one or several units or devices may be performed by any other number of units or devices. The procedures and/or the control of the X-ray imaging system in accordance with the method for determining a catheter position and the procedure of navigating the catheter can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. An X-ray imaging system, comprising:
   a robotic catheter, and a processor, the processor being connectable to an X-ray image data source for receiving X-ray image data of a patient environment and connectable to the robotic catheter, wherein the processor is adapted to:
   a) receive one or more auxiliary information items received from at least one of the X-ray image data source and the robotic catheter; and
   b) at a time t, determine a set of three-dimensional orientations and positions of the robotic catheter relative to the patient environment as a function of the X-ray image data and the one or more auxiliary information items, wherein the processor is adapted to:
   c) i) process the set of three-dimensional orientations and positions of the robotic catheter relative to the patient environment as a function of two-dimensional image data and the one or more auxiliary information items into an image based set of steering commands, and ii) provide the image based set of steering commands as feedback to the robotic catheter; and
   d) i) render an image of the set of three-dimensional orientations and positions, and at least one of the X-ray image data and a three-dimensional representation of the patient environment, and provide the image to a visualization device, ii) receive user input representing a user choice of one of the set of three-dimensional orientations and positions of the robotic catheter relative to the patient environment displayed by the visualization device, iii) process the user input into a user based set of steering commands, and iv) provide the user based set of steering commands as feedback to the robotic catheter.

2. The X-ray imaging system according to claim 1, wherein the one or more auxiliary information items represent at least one of:
   a curvature of at least a portion of the robotic catheter,
   a steering command previously transmitted to the robotic catheter,
   a previous orientation of the robotic catheter,
   a previous position of the robotic catheter,
   a previous curvature of at least a portion of the robotic catheter,
   a force feedback signal detected and transmitted by the robotic catheter, and anatomical boundary information from the three-dimensional representation of the patient environment.

3. The X-ray imaging system according to claim 1, wherein an additional user input represents one or more commands for moving the robotic catheter.

4. The X-ray imaging system according to claim 1, wherein a tip of the robotic catheter is adapted to perform movements along a predetermined path, and the processor is adapted to detect the movements from a series of two-dimensional X-ray image data of the patient environment and to deduce therefrom the orientation of the robotic catheter.

5. The X-ray imaging system according to claim 1, wherein a tip of the robotic catheter comprises multiple radio-opaque markers, which are arranged symmetrically or asymmetrically along the tip of the robotic catheter in a fixed spatial relation to wires for steering the robotic catheter in order to deduce therefrom the orientation of the robotic catheter.

6. The X-ray imaging system according to claim 1, wherein the processor is adapted to initialize the determination of the set of three-dimensional orientations and positions of the robotic catheter based upon two or more two-dimensional images obtained by the X-ray image data source and to track the set of three-dimensional orientations and positions being determined.

7. The X-ray imaging system according to claim 1, wherein a determination by the processor at the time t of the set of three-dimensional orientations and positions of the robotic catheter relative to the patient environment as the function of the X-ray image data and the one or more auxiliary information items comprises: transposing, at the time t, a curvature of the robotic catheter as indicated by the one or more auxiliary information items to a curvature of the robotic catheter as represented by the X-ray image data.

8. The X-ray imaging system of claim 1, wherein the user based set of steering commands for moving the robotic catheter are displayed in display or image coordinates on the visualization device.

9. The X-ray imaging system of claim 8, wherein the user based set of steering commands cause the robotic catheter to bend left, right, up, down, front or back, with respect to the image, which is being displayed by the visualization device.

10. The X-ray imaging system of claim 8, wherein the user based set of steering commands provided to the robotic catheter are translated by the processor from display coordinates into coordinates in a catheter system.

11. A processor connected to a tangible, non-transitory computer-readable storage medium storing a computer program for operating an X-ray imaging system comprising a robotic catheter, the computer program comprising instructions for determining an orientation and position of the robotic catheter inside a patient environment, wherein when executed by the processor, the instructions cause the processor to:
   a) obtain X-ray image data of the patient environment and the robotic catheter from an X-ray image data source,
   b) obtain one or more auxiliary information items from at least one of the robotic catheter and the X-ray image data source,
   c) at a time t, determine a set of three-dimensional orientations and positions of the robotic catheter relative to the patient environment as a function of the X-ray image data and the one or more auxiliary information items,
   d) i) process the set of three-dimensional orientations and positions of the robotic catheter relative to the patient environment as a function of two-dimensional image data and the one or more auxiliary information items into an image based set of steering commands, and ii) provide the image based set of steering commands as feedback to the robotic catheter; and
   e) i) render an image of the set of three-dimensional orientations and positions, and at least one of the X-ray image data and a three-dimensional representation of the patient environment, and providing the image to a visualization device, ii) receive user input representing a user choice of one of the set of three-dimensional orientations and positions of the robotic catheter relative to the patient environment displayed by the visualization device, iii) process the user input into a user based set of steering commands, and iv) provide the user based set of steering commands as feedback to the robotic catheter.

12. The processor according to claim 11, wherein when executed by the processor, the instructions further cause the processor to:
   perform movements of a tip of the robotic catheter along a predetermined path,
   detect the movements in a series of X-ray image data, and
   deduce the orientation of the tip of the robotic catheter from the movements.

13. The processor according to claim 11, wherein the determination at the time t of the set of three-dimensional orientations and positions of the robotic catheter relative to the patient environment as the function of the X-ray image data and the one or more auxiliary information items comprises further instructions, which when executed by the processor, cause the processor to:
   transpose, at the time t, a curvature of the robotic catheter as indicated by the one or more auxiliary information items to a curvature of the robotic catheter as represented by the X-ray image data.

14. The processor of claim 11, wherein the user based set of steering commands for moving the robotic catheter are displayed in display or image coordinates on the visualization device.

15. The processor of claim 14, wherein the user based set of commands cause the robotic catheter to bend left, right, up, down, front or back, with respect to the image, which is being displayed by the visualization device.

16. The processor of claim 14, wherein the user based set of steering commands provided to the robotic catheter are translated by the processor from display coordinates into coordinates in a catheter system.

17. The processor of claim 11, wherein a tip of the robotic catheter comprises multiple radio-opaque markers, which are arranged symmetrically or asymmetrically along the tip of the robotic catheter in a fixed spatial relation to wires for steering the robotic catheter in order to deduce therefrom the orientation of the robotic catheter.

18. A tangible, non-transitory computer-readable storage medium that stores machine executable instructions executable on a processor for operating an X-ray imaging system comprising a robotic catheter, wherein when executed by the processor, the machine executable instructions cause the processor to:
   a) obtain X-ray image data of a patient environment and the robotic catheter from an X-ray image data source,
   b) obtain one or more auxiliary information items from at least one of the robotic catheter and the X-ray image data source,
   c) at a time t, determine a set of three-dimensional orientations and positions of the robotic catheter relative to the patient environment as a function of the X-ray image data and the one or more auxiliary information item or items,
   d) i) process a three dimensional orientation and position of the set of the three-dimensional orientations and positions of the robotic catheter relative to the patient environment as a function of two-dimensional image data and the one or more auxiliary information items into an image based set of steering commands, and ii)

provide the image based set of steering commands as feedback to the robotic catheter; and
e) i) render an image of the set of three-dimensional orientations and positions, and at least one of the X-ray image data and a three-dimensional representation of the patient environment, and provide the image to a visualization device, ii) receive user input representing a user choice of one of the set of three-dimensional orientations and positions of the robotic catheter relative to the patient environment displayed by the visualization device, iii) process the user input into a user based set of steering commands, and iv) provide the user based set of steering commands as feedback to the robotic catheter.

19. The tangible, non-transitory computer-readable medium of claim 18, wherein when executed by the processor, the machine executable instructions further cause the processor to:
perform movements of a tip of the robotic catheter along a predetermined path,
detect the movements in a series of X-ray image data, and
deduce the orientation of the tip of the robotic catheter from the movements.

20. The tangible, non-transitory computer-readable medium of claim 18,
wherein the determination at the time t of the set of three-dimensional orientations and positions of the robotic catheter relative to the patient environment as the function of the X-ray image data and the one or more auxiliary information items the tangible, non-transitory computer-readable medium comprises further instructions, which when executed by the processor, cause the processor to:
transpose, at the time t, a curvature of the robotic catheter as indicated by the one or more auxiliary information items to a curvature of the robotic catheter as represented by the X-ray image data.

21. The tangible, non-transitory computer-readable medium of claim 18, wherein the user based set of steering commands for moving the robotic catheter are displayed in display or image coordinates on the visualization device.

22. The tangible, non-transitory computer-readable medium of claim 21, wherein the user based set of steering commands cause the robotic catheter to bend left, right, up, down, front or back, with respect to the image, which is being displayed by the visualization device.

23. The tangible, non-transitory computer-readable medium of claim 21, wherein the user based set of steering commands provided to the robotic catheter are translated by the processor from display coordinates into coordinates in a catheter system.

24. The tangible, non-transitory computer-readable medium of claim 18, wherein a tip of the robotic catheter comprises multiple radio-opaque markers, which are arranged symmetrically or asymmetrically along the tip of the robotic catheter in a fixed spatial relation to wires for steering the robotic catheter in order to deduce therefrom the orientation of the robotic catheter.

\* \* \* \* \*